(12) United States Patent
Xia et al.

(10) Patent No.: US 10,159,663 B2
(45) Date of Patent: Dec. 25, 2018

(54) SUBSTITUTED MACROCYCLES USEFUL AS KINASES INHIBITORS AND METHODS OF USE THEREOF

(71) Applicant: TELIGENE LTD., Suzhou (CN)

(72) Inventors: Xiaoyang Xia, Thousand Oaks, CA (US); Dawei Zhang, Thousand Oaks, CA (US)

(73) Assignee: Teligene Ltd., Suzhou (CN)

( * ) Notice: Subject to any disclaimer, the term of this patent is extended or adjusted under 35 U.S.C. 154(b) by 0 days.

(21) Appl. No.: 15/500,927

(22) PCT Filed: Aug. 18, 2015

(86) PCT No.: PCT/CN2015/087343
§ 371 (c)(1),
(2) Date: Jan. 31, 2017

(87) PCT Pub. No.: WO2016/026423
PCT Pub. Date: Feb. 25, 2016

(65) Prior Publication Data
US 2017/0216264 A1 Aug. 3, 2017

Related U.S. Application Data

(60) Provisional application No. 62/070,250, filed on Aug. 20, 2014.

(51) Int. Cl.
*A61K 31/439* (2006.01)
*C07D 498/18* (2006.01)
*A61P 35/00* (2006.01)

(52) U.S. Cl.
CPC ............ *A61K 31/439* (2013.01); *A61P 35/00* (2018.01); *C07D 498/18* (2013.01)

(58) Field of Classification Search
CPC ............................ C07D 498/18; A61K 31/439
USPC ........................................................ 514/286
See application file for complete search history.

(56) References Cited

U.S. PATENT DOCUMENTS 9,637,500 B2 * 5/2017 Jensen ................. C07D 498/18

FOREIGN PATENT DOCUMENTS

WO WO-2011138751 A2 * 11/2011 ........... C07D 401/04
WO WO-2013132376 A1 * 9/2013 ........... C07D 491/08

* cited by examiner

*Primary Examiner* — Rita J Desai
(74) *Attorney, Agent, or Firm* — Feng Tian

(57) ABSTRACT

The present invention is directed to novel substituted macrocycles compounds, pharmaceutically acceptable salts, solvates and hydrates thereof. The compounds and compositions of the present invention have protein kinases inhibitory activities and are expected to be useful for the treatment of protein kinases mediated diseases and conditions.

7 Claims, No Drawings

SUBSTITUTED MACROCYCLES USEFUL AS KINASES INHIBITORS AND METHODS OF USE THEREOF

CROSS REFERENCE

This invention claims the benefit of U.S. Provisional Patent Application No. 62/070,250, filed on Aug. 20, 2014, which is incorporated herein by reference in its entirety.

FIELD OF THE INVENTION

The present invention is directed to inhibitors of kinase and pharmaceutically acceptable salts, solvates, hydrates, prodrugs and metabolites thereof, the preparation method thereof, and the use of such compounds to treat kinase mediated diseases and conditions such as cancer.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. Examples of kinases in the protein kinase family include, without limitation, Abl1 (v-Abl Abelson murine leukemia viral oncogene homolog 1), Akt, Alk, Bcr-Abl1, Blk, Brk, Btk, c-Kit, c-Met, c-Src, c-Fms, CDK1-10, b-Raf, c-Raf1, CSF1R, CSK, EGFR, ErbB2, ErbB3, ErbB4, Erk, FGFR1, FGFR2, FGFR3, FGFR4, FGFR5, Flt-1, Fps, Frk, Jak, KDR, MEK, PDGFR, PIK, PKC, PYK2, Ros, Tie, Tie2, and Zap70. Due to their activity in numerous cellular processes, protein kinases have emerged as important therapeutic targets.

ALK (Anaplastic Lymphoma Kinase) is a 1620 amino acid transmembrane protein, consisting of extracellular domain with amino-terminal signal peptide, intracellular domain with a juxtamembranous segment harboring a binding site for insulin receptor substrate-1, and a carboxy-terminal kinase domain. ALK is a member of the insulin receptor tyrosine kinases. Echinoderm microtubule-associated protein-like 4 (EML4) is a 120 KDa cytoplasmic protein, which involves in the formation of microtubules and microtubule binding protein. EML4-ALK is a novel fusion gene arising from an inversion on the short arm of chromosome 2 that joined exons 1-13 of EML4 to exons 20-29 of ALK. The presence of EML4-ALK fusion is identified in approximately 3-13% of NSCLC (non-small cell lung cancer) patients.

To this end, attempts have been made to identify small molecules which act as protein kinases inhibitors. For example, amino heteroaryl compounds diaryl ureas (PCT WO2004/076412) have been described as ALK/c-MET inhibitors.

Epidermal growth factor (EGF) is a widely distributed growth factor that in cancer, can stimulate cancer-cell proliferation, block apoptosis, activate invasion and metastasis, and stimulate angiogenesis (Citri, et al., *Nat. Rev. Mol. Cell. Biol.* 7:505, 2006; Hynes, et al., *Nat. Rev. Cancer* 5:341, 2005). The EGF receptor (EGFR or ErbB) is a transmembrane, tyrosine kinase receptor that belongs to a family of four related receptors. The majority of human epithelial cancers are marked by functional activation of growth factors and receptors of this family (Ciardiello, et al., *New Eng. J. Med.* 358: 1160, 2008) so that EGF and EGFR are natural targets for cancer therapy. The human epidermal growth factor receptor (HER) tyrosine kinase family consists of four structurally related cellular receptors: the epidermal growth factor receptor (EGFR; HER1), HER2 (ErbB2), HER3 (ErbB3), and HER4.

Thus, the compounds that can inhibit protein kinases such as ALK, ROS1, or EGFR kinases activity together can be used to treat human diseases such as cancers.

SUMMARY OF THE INVENTION

The present invention provides compounds of Formula I:

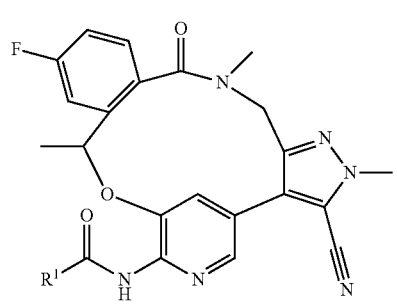 [SMILES: CC(=O)Nc1ncc2cc1O[C@H](C)c1cc(F)ccc1C(=O)N(C)Cc1nn(C)c(C#N)c1-2]

I or a pharmaceutically acceptable salt, solvate or a prodrug or an enantiomer, or a metabolite thereof, wherein
$R^1$ is $C_{1-6}$ alkyl or $NH_2(R^2R^3)C-$;
$R^2$ and $R^3$ are independently H or $C_{1-6}$ alkyl.

The present invention further provides pharmaceutical compositions comprising a compound of Formula I described above and a pharmaceutically acceptable carrier.

The present invention further provides methods for treating or preventing a kinase mediated disorder comprising administrating to a mammalian subject a therapeutically effective amount of any of the compounds of Formula I described above.

DETAILED DESCRIPTION OF THE INVENTION

In some embodiments of the present invention, there are provided compounds of Formula I:

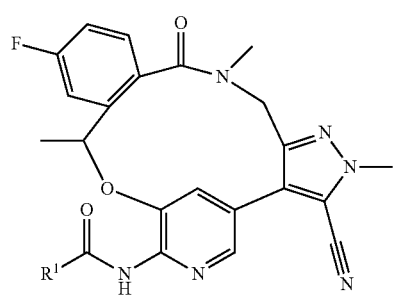

I or a pharmaceutically acceptable salt, solvate or an enantiomer, or a prodrug or a metabolite thereof, wherein
$R^1$ is $C_{1-6}$ alkyl, or $NH_2(R^2R^3)C-$;
$R^2$ and $R^3$ are independently H or $C_{1-6}$ alkyl;
In certain embodiments, there are provided compounds without limitation selected from the group consisting of:

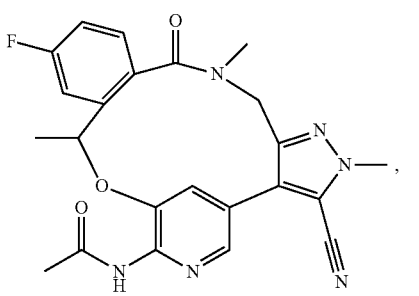

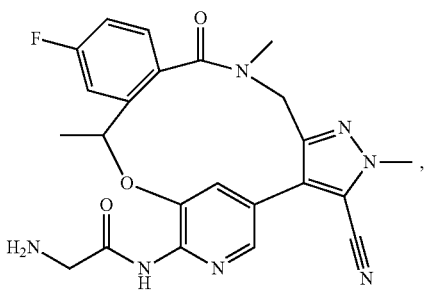

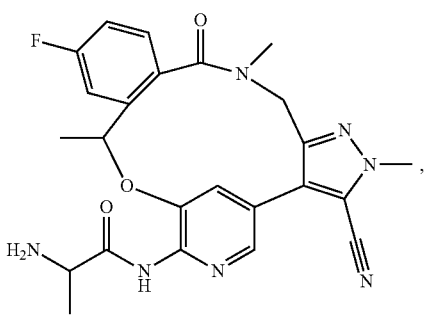

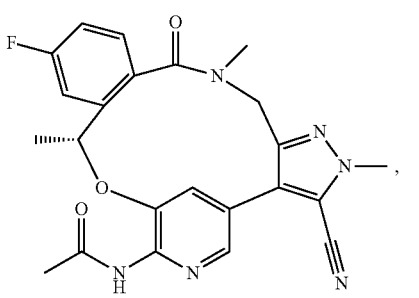

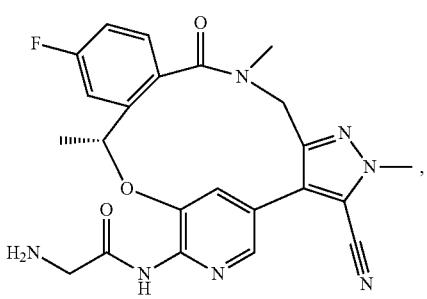

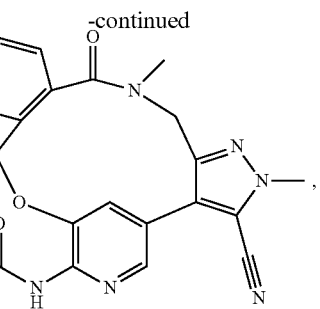

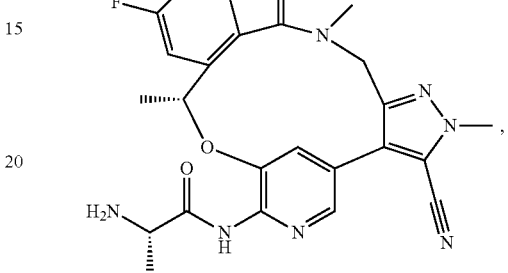

and the like, or a pharmaceutically acceptable salt, solvate, or a prodrug, or a metabolite thereof.

In other embodiments, the compound of this invention is in the form of a metabolite. In other embodiments, the compound of this invention is in the form of a prodrug. In some embodiments, the compound of this invention is an enantiomer. In other embodiments, the compound of this invention is a diastereomer. In another embodiment, the deuterium enrichment in compounds of this invention is at least about 1%.

In some embodiments, there are provided pharmaceutical compositions comprising a compound of the invention and a pharmaceutically acceptable carrier. In certain embodiments, the compositions are for the treatment of a disease regulated by a protein kinase. In certain embodiments, the compositions are for the prevention or the treatment of a hyper-proliferative disorder and/or angiogenesis disorder. In other embodiments, the pharmaceutical compositions are suitable for oral, parenteral, or intravenous administration.

In some embodiments, the present invention provides methods for regulating the kinase signaling transduction, said method comprises administrating to a mammalian subject a therapeutically effective amount of any of the inventive compounds described herein.

In other embodiments provide herein methods for treating or preventing an ALK, ROS1, and/or EGFR (including all fusion and/or mutant kinases) mediated disorder, said method comprises administrating to a mammalian subject a therapeutically effective amount of any of the inventive compounds described herein.

In some embodiments, the present invention provides methods for treating neoplasia.

In other embodiments, the present invention provides methods for treating cancer diseases, including but not limited to, lung cancer, breast cancer, brain cancer, chronic lymphocytic leukemia, mantle cell lymphoma, and diffuse large B-cell lymphoma.

In some embodiments, there are provided pharmaceutical compositions comprising a compound of the present invention in combination with one or more anti-cancer agents for treating neoplasia.

In other embodiments, the present invention provides methods for treating or preventing of a hyper-proliferative disorder.

The following definitions should assist in understanding the invention described herein.

The term "alkyl" is intended to include straight, branched, and cyclic hydrocarbon groups, which contain only single carbon-carbon bonds and which may be unsubstituted or optionally substituted with one or more functional groups. The preferred chain length of an alkyl group is from 1 to 6 carbon atoms. $C_1$-$C_6$ alkyl is intended to include $C_1$ (methyl), $C_2$ (ethyl), $C_3$ (n-propyl, isopropyl), $C_4$ (e.g. n-butyl, isobutyl, sec-butyl, tert-butyl), $C_5$ (e.g. n-pentyl) and $C_6$ alkyl groups. Alkyl may be substituted or unsubstituted. Illustrative substituted alkyl groups include, but are not limited to, fluoromethyl, difluoromethyl, trifluoromethyl, aminomethyl, aminoethyl, hydoxymethyl, methoxymethyl, 2-fluoroethyl, and 2-methoxyethyl, etc.

The term "pharmaceutically acceptable" when used with reference to a compound of the invention is intended to refer to a form of the compound that is safe for administration to a subject. For example, a free base, a salt form, a solvate, a hydrate, a prodrug or derivative form of a compound of this invention, which has been approved for mammalian use, via oral ingestion or any other route of administration, by a governing authority or regulatory agency, such as the Food and Drug Administration (FDA) of the United States, is pharmaceutically acceptable.

The phrase "effective amount" is intended to quantify the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

Starting materials of the invention, are either known, commercially available, or can be synthesized in analogy to or according to methods that are known in the art. Many starting materials may be prepared according to known processes and, in particular, can be prepared using processes described in the examples. While synthesizing starting materials, functional groups in some cases are protected with suitable protecting groups when necessary. Protecting groups, their introduction and removal are described hereinafter.

In synthesizing a compound of formulas I according to a desired procedure, the steps in some embodiment, are performed in an order suitable to prepare the compound, including a procedure described herein or by an alternate order of steps described herein, and in one embodiment, be preceded, or followed, by additional protection/deprotection steps as necessary. The intermediates in some embodiments are isolated or carried on in situ, with or without purification. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2$^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, 2$^{nd}$ edition, Wiley-VCH, (1997); and L. Paquette, editor, Encyclopedia of Reagents for Organic Synthesis, John Wiley and Sons (1995).

The compounds of this invention in some embodiments also are represented in multiple tautomeric forms. The invention expressly includes all tautomeric forms of the compounds described herein.

The compounds in one embodiment also occur in cis- or trans- or E- or Z-double bond isomeric forms. All such isomeric forms of such compounds are expressly included in the present invention.

Indication

The present invention provides compounds which are capable of modulating one or more signal transduction pathways comprising, but not limited to ALK, ROS1, and EGFR.

By the term "modulating," it is meant that the functional activity of the pathway (or a component thereof) is changed in comparison to its normal activity in the absence of the compound. This effect includes any quality or degree of modulation, including, increasing, agonizing, augmenting, enhancing, facilitating, stimulating, decreasing, blocking, inhibiting, reducing, diminishing, antagonizing, etc.

The compounds of the present invention can also modulate one or more of the following processes, including, but not limited to, e.g., cell growth (including, e.g., differentiation, cell survival, and/or proliferation), tumor cell growth (including, e.g., differentiation, cell survival, and/or proliferation), tumor regression, endothelial cell growth (including, e.g., differentiation, cell survival, and/or proliferation), angiogenesis (blood vessel growth), lymphangiogenesis (lymphatic vessel growth), and/or hematopoiesis (e.g., T- and B-cell development, dendritic cell development, etc.).

While not wishing to be bound by any theory or mechanism of action, it has been found that compounds of the present invention possess the ability to modulate kinase activity. The methods of the present invention, however, are not limited to any particular mechanism or how the compounds achieve their therapeutic effect. By the phrase "kinase activity," it is meant a catalytic activity in which a gamma-phosphate from adenosine triphosphate (ATP) is transferred to an amino acid residue (e.g., serine, threonine, or tyrosine) in a protein substrate. A compound can modulate kinase activity, e.g., inhibiting it by directly competing with ATP for the ATP-binding pocket of the kinase, by producing a conformational change in the enzyme's structure that affects its activity (e.g., by disrupting the biologically-active three-dimensional structure), by binding to and locking the kinase in an inactive conformation, etc.

Formulations and Method of Use

The amount of compound(s) which is/are administered and the dosage regimen for treating cancer with the compounds and/or compositions of this invention depend on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, even more advantageously between about 0.1 and about 10 mg/kg may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients, adjuvants and the like (collectively referred to herein as "carrier" materials) as described herein, and, if desired, other active ingredients. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nanoparticulates, gels, solid solution, liposome, films (including muco-adhesive), ovules, sprays and liquid formulations.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

Synthesis

The compounds of Formula I were synthesized according to the procedures described in the following Schemes to those skilled in the art, wherein the substituents are as defined for Formula I above, except where further noted. The synthetic methods described below are merely exemplary, and the compounds of the invention may also be synthesized by alternate routes as appreciated by persons of ordinary skill in the art.

The synthesis of compounds in the invention was described in the following Scheme 1.

Compounds described in Formula I are synthesized with literature known starting materials Compound A (PF-06463922) and Compound B. The reaction of Compound A and Compound B in solvent such as dichloromethane with base such as pyridine generates compounds of Formula I.

Scheme 1

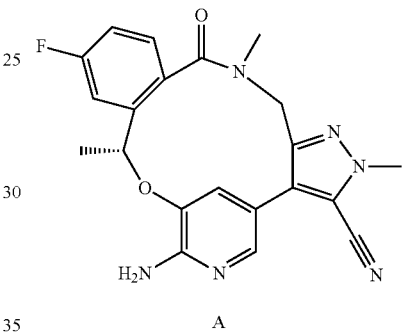

A

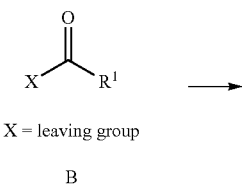

X = leaving group

B

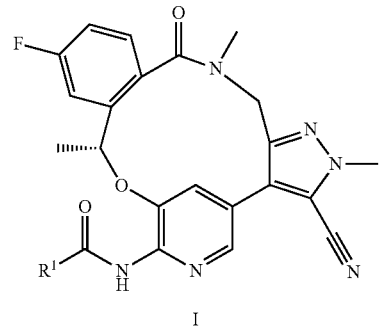

I

Compound 6 is synthesized using the procedure described in Scheme 2. The acylation of Compound 1 affords Compound 2, which couples with Compound 3 with n-propyl-phosphonoic anhydride (T3P) to generate Compound 4. Intramolecular cyclization under palladium catalyzed condition to give Compound 5. Deprotection of Fmoc group leads to the synthesis of Compound 6 (Scheme 2).

Scheme 2
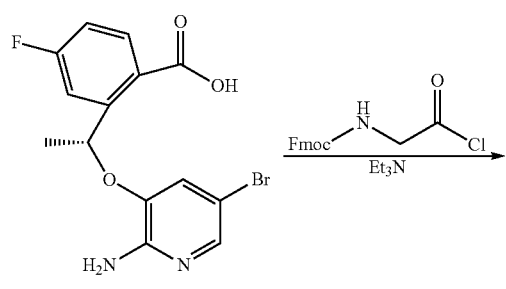
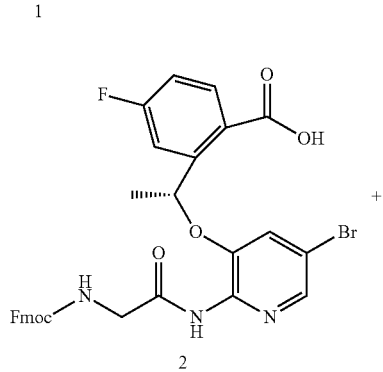
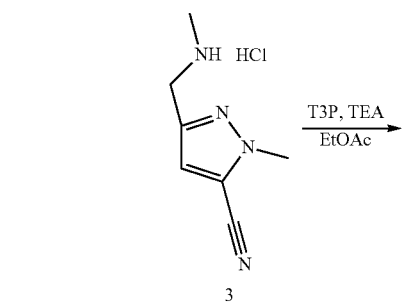
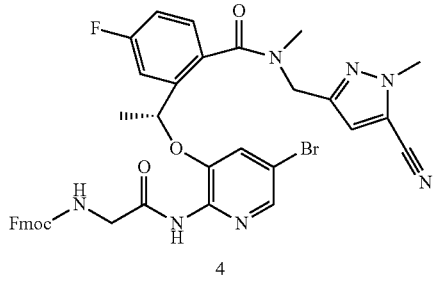
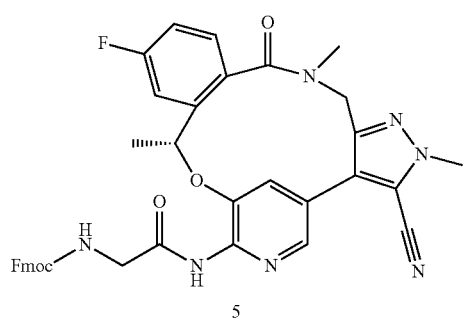
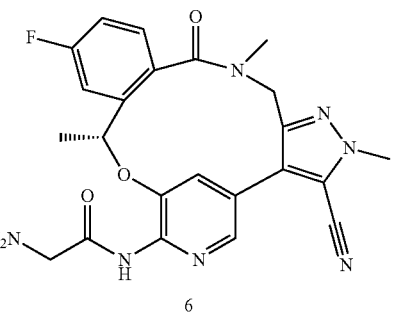
Alternatively, Compound 6 is synthesized using the procedure described in Scheme 3. The acylation of Compound 7 affords Compound 8. Deprotection of the Boc group to afford Compound 9, which undergoes intramolecular amide formation to generate Compound 5. Deprotection of Fmoc group of Compound 5 leads to the synthesis of Compound 6 (Scheme 3).
Scheme 3
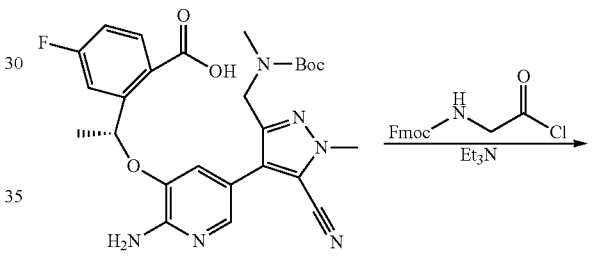
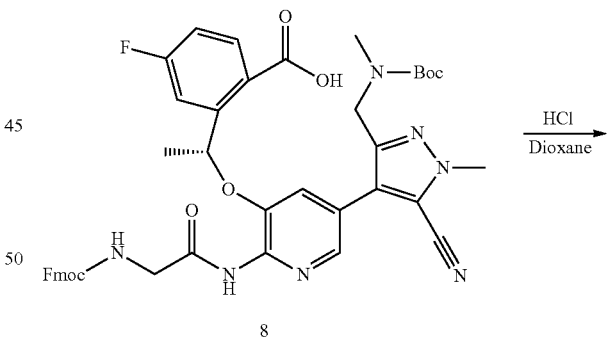

-continued

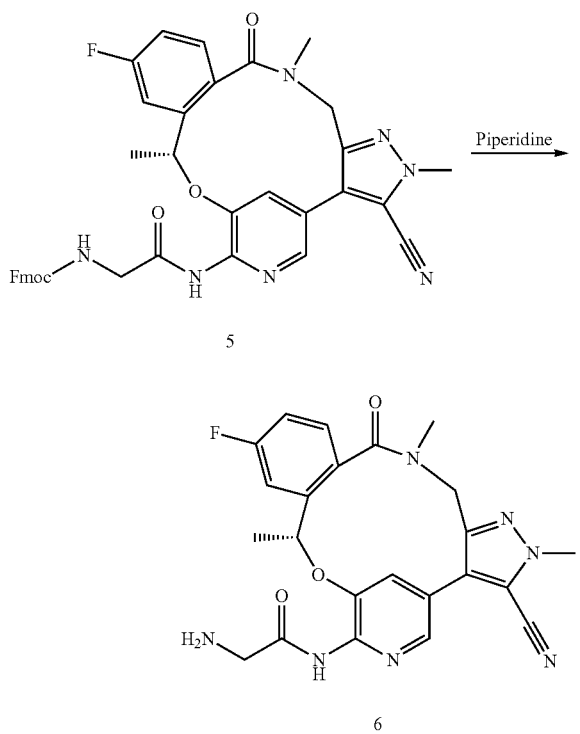

5

6

Proton NMR Spectra

Unless otherwise indicated, all $^1$H NMR spectra were run on a Varian series Mercury 300, 400, 500 MHz instrument or a Bruker series 400, 500 MHz instrument. Where so characterized, all observed protons are reported as parts-per-million (ppm) downfield from tetramethylsilane (TMS) or other internal reference in the appropriate solvent indicated.

Abbreviations

DMF means N,N-dimethylformamide.

DCM means dichloromethane.

DIPEA means diisopropyl ethylamine.

DCC means Dicyclohexylcarbodiimide.

THF means tetrahydrofuran.

EA means ethyl acetate.

m-CPBA means meta-Chloroperoxybenzoic acid.

Boc-Gly-OH means N-(tert-Butoxycarbonyl)glycine.

BOP means (Benzotriazol-1-yloxy)tris(dimethylamino)phosphonium hexafluorophosphate.

Pd(dppf)Cl$_2$ means [1,1'-Bis(diphenylphosphino)ferrocene]dichloropalladium.

T3P means n-propylphosphonoic anhydride

Et$_3$N means triethyl amine

Fmoc means Fluorenvlmethyloxycarbonyl cataCXium means Di(1-adamantyl)-n-butylphosphine Pd(OAc)$_2$ means palladium acetate CYP means Cytochrome P450

EGFR means epidermal growth factor receptor

ERBB4 means receptor tyrosine-protein kinase erbB-4

Example 1: The synthesis of (10R)-7-acetamido-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (Compound 10)

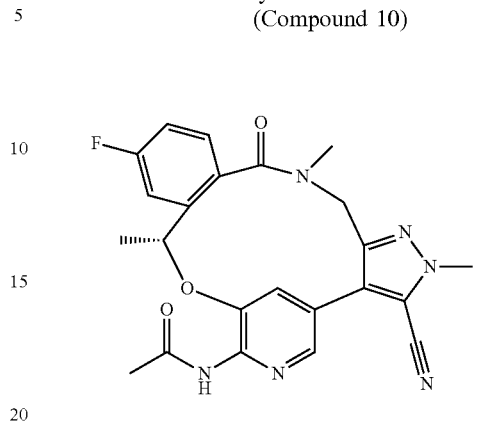

To a solution of (10R)-7-amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (50 mg) in THF (2 mL) was added pyridine (189.6 mg, 10.0 eq) at 0° C. and stirred for 0.5 h, then acetyl chloride (150.4 mg, 8.0 eq) was added portionwise. The reaction was stirred for 4 hours at 0° C., and TLC indicated the completion of the reaction. Water (20 mL) was added to the reaction, and the aqueous layer was extracted with EA (2×10 mL). The organic layers were combined, washed with brine (20 mL), dried over anhydrous sodium sulfate. The crude product was purified by preparative TLC plate to give white solid (15 mg) as Compound 10. 1H-NMR (400 MHz, CDCl$_3$): 8.13 ppm, (d, J=1.6 Hz, 1H), 8.04 (s, 1H), 7.31 (dd, J$_1$=2.8 Hz, J$_2$=9.6 Hz, 1H), 7.25 (m, 1H), 7.06 (m, 2H), 5.79 (m, 1H), 4.13 (s, 3H), 3.16 (s, 3H), 2.59 (s, 3H), 1.83 (d, J=6.0 Hz, 3H). MS m/z 449 [M+1].

Example 2: The synthesis of (10R)-7-(2-aminoacetyl)amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (Compound 6)

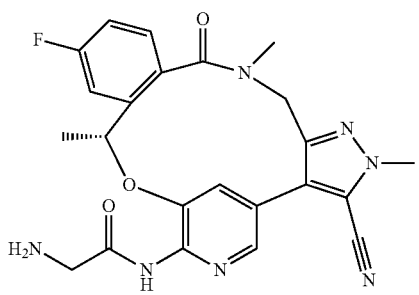 [SMILES: C[C@H]1Oc2cc(cnc2NC(=O)CN)-c2c(nn(C)c2C#N)CN(C)C(=O)c2ccc(F)cc21]

The Fmoc-glycine (763.4 mg, 2.6 mmol, 20.0 eq) was added into SOCl$_2$ (16.0 mL) and the mixture was heated to reflux for 2 h. Evaporation in vacuum to give a white solid. The solid was dissolved in DCM (8.0 mL), and a solution of (10R)-7-amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (Compound A, 50.0 mg, 0.13 mmol, 1.0 eq) in pyridine (16.0 mL) was added in two portions. The reaction mixture was stirred for 16 hours at RT. Then water (20 mL) was added. The aqueous lay was extracted with DCM (2×10 mL), and the organic layers were combined, dried over anhydrous sodium sulfate, filtered and concentrated. The crude was purified by preparative TLC plate to give compound 5 (30 mg). To a solution of Compound 5 (30.0 mg) in DCM (2.0 mL) was added piperidine (0.1 mL) at 0° C. The reaction was stirred 5 hours at RT and TLC indicated the completion of the reaction. The reaction mixture was concentrated and washed with n-Hexane (2×5 mL) to give crude product. Then the crude product was purified by flash column chromatography on silica gel (the silica gel was pre-washed with 1% $Et_3N$ in DCM) with DCM/MeOH (100:1) to give Compound 6 (12.3 mg). $^1$H-NMR (400 MHz, $CDCl_3$): 8.23 ppm. (s, 1H), 7.31 (m, 1H), 7.25 (m, 1H), 7.14 (d, J=2.0 Hz, 1H), 7.04 (m, 2H), 5.80 (m, 1H), 4.46 (m, 2H), 4.12 (s, 3H), 3.78 (s, 2H), 3.17 (s, 3H), 1.85 (d, J=6.0 Hz, 3H). MS m/z: 464 [M+1].

Biological Assays:

As stated hereinbefore, the compounds defined in the present invention possess anti-proliferation activity. These properties may be assesses, for example, using one or more of the procedures set out below:

An In Vitro Assay which Determines the Ability of a Test Compound to Inhibit Kinase:

Kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

The following Table A lists a compound representative of the invention and its inhibition activity in kinases assays.

TABLE A

| Kinase Inhibition | |
|---|---|
| Kinase | Compound 6 |
| EGFR(L747-E749del, A750P) | 0.4 μM |
| ERBB4 | 5.7 μM |

The Compound 6 is a potent inhibitor (420 nM) for a mutant EGFR (L747-E749del, A750P).

A Representative Number of Compounds were Assayed Against Different Cancer Cell Lines Such as HCC827 and NCI-H69 Using the Cell Proliferation Assays:

Cell Proliferation Assays:

1. $5×10^3$ cells per well in 100 μl of medium were seeded in 96-well plate, while the medium here contained 5% FBS.

2. 24 hours later, 100 μl fresh medium was added with various concentrations of compounds into each well, while the medium here was free of FBS.

3. After the cells were treated with compounds for 72 hours, 20 μl MTT (5 mg/ml) was added into each well, and then the assay plate was incubated at 37° C. for 4 more hours.

4. The assay plate was centrifuged at 800 g for 10 min. The medium was aspirated, 150 μl DMSO was added into each well. The plate was gently shaken for 10 min.

5. The absorbance at 570 nm was measured on the plate reader.

6. IR %=(WC−WT)/WC*100%.

The following Table B lists compounds representative of the invention and their activity in cell assays.

TABLE B

| Cell proliferation Assays. | | |
|---|---|---|
| Compound | HCC827 Cell ($IC_{50}$) | NCI-H69 Cell ($IC_{50}$) |
| 6 | 65.57 μM | 77.12 μM |

A Representative Number of Compounds were Tested in P450 3A4 Assay in Human Liver Microsomes to Measure CYP Inhibition:

Human liver microsomes (HLM) are stored at −80° C. Before the study, microsomes were thawed in a cold water bath, and then were put on ice immediately. Test compounds and P450 3A4 specific inhibitor ketoconazole were dissolved in DMSO to yield stock solution of 10 mM. The stock solution was diluted with 50% acetonitrile to get working solution at the concentration of 1.5 mM. The working solution was further diluted with 0.1 M potassium phosphate buffer to get a series of working solution at concentrations of 150, 50, 15, 5, 1.5, 0.5, 0.15, and 0.05 μM. Incubation mixtures in duplicate contain pooled human liver microsome (0.1 mg/mL), 3.3 mM $MgCl_2$, CYP 3A4 probe substrate testosterone (50 μM), specific inhibitor or test compounds (30, 10, 3, 0.1, 0.03, 0.01, 0.003, 0.01 μM) in 0.1 M potassium phosphate buffer (total volume 0.1 mL). Negative control contains 0.1 M phosphate buffer instead of specific inhibitor or test compound. The final concentrations of DMSO and acetonitrile were equal or less than 0.1%. The mixtures are pre-incubated for 10 min at 37° C. Then, 1 mM NADPH is added to initiate reaction. Following a 10-min incubation at 37° C., the reactions are terminated by the addition of 300 μL acetonitrile containing an internal standard. The formation of the corresponding products is detected by LC/MS/MS.

LCMS method: A Waters ACQUITY UPLC system coupled API 4000 Qtrap system was used. The mass spectrometer is equipped with Turbo Ion Spray (ESI) Interface (Applied Biosystems, Concord, Ontario, Canada). Analyst 1.5 software packages (Applied Biosystems) were used to control the LC-MS/MS system, as well as for data acquisition and processing. Chromatographic separation was achieved on Waters ACQUITY UPLC BEH C18 column (50×2.1 mm ID, 1.7 μm). The column temperature was maintained at ambient temperature (25° C.). The mobile phase A is pure water supplemented with 0.1% formic acid (v/v). The mobile phase B is acetonitrile supplemented with 0.1% formic acid (v/v). The flow rate was maintained at 0.6 mL/min.

Sample Preparation: The reactions were quenched by the addition of 3-fold volume of ice-cold methanol/acetonitrile (1/1, v/v) mix containing an internal standard. The mixture was centrifuged at 4000 rpm for 20 min. 100 μL of supernatant were mixed with 200 μL of $H_2O$ and the final solution were injected for LC-MS/MS analysis.

Data Analysis: The peak area ratio of product (6β-hydroxytestosterone) to internal standard is plotted as a percentage of the relevant negative control for each reaction to represent the residual enzymatic activity. The IC50 value of a test compound is determined by nonlinear regression of a plot enzymatic activity versus inhibitor concentration using GraphPad Prism software. The general criteria to evaluate the potential risk of drug-drug interaction (DDI) is as followed:

IC50>10 μM CYP inhibition low;
3 μM<IC50<10 μM CYP inhibition moderate
IC50<3 μM CYP inhibition high The following Table C lists compounds representative of the invention and their activity in Cytochrome P450 3A4 Assay.

TABLE C

| CYP 3A4 inhibition | |
|---|---|
| Compound | CYP 3A4 ($IC_{50}$) |
| A (PF-06463922) | 7.8 μM |
| 6 | 10 μM |
| 10 | 14 μM |

Compound PF-06463922 showed moderate Cytochrome P450 3A4 inhibition. Compound 6 and 10 showed low Cytochrome P450 3A4 inhibition, which indicates they have better safety profiles.

A Representative Number of Compounds were Tested in Rat Whole Blood to Measure Rate of Metabolism.

Preparation of Stock Solutions: Stock solution of test compound was provided in 100% DMSO. The stock solution for each compound was diluted into 500 μM with a mixture of acetonitrile: PBS buffer (2:8) and then diluted into rat blood (pH 7.4) to achieve a final concentration of 1.0 μM.

Incubation: 1.0 μM of test compound in duplicate was incubated in blood at 37° C. Aliquots of 50 μL sample were collected at 0 h, 0.25 h, 0.5 h, 1 h, and 2 h.

Sample preparation: Reactions were terminated at various time points (0, 0.25, 0.5, 1, 2 h) by adding 150 μL of ice-cold acetonitrile containing an internal standard. Centrifuge the plate (4000 rpm, 15 min). 100 μL of supernatants were transferred into a daughter plate containing 200 μL of $H_2O$ and 0.1% formic acid (v/v) in each well. The samples were analyzed with UPLC-MS/MS.

Data analysis: The peak area ratio of test compound to internal standard is plotted as a percentage of the relevant zero time point control (% Remained) for each reaction. The rate of metabolism (k) is the slope of the linear regression from log percentage remaining versus incubation time. The T½ is calculated as −0.693/k.

The following Table D lists compounds representative of the invention and their rate of metabolism (k) in in Rat whole blood.

TABLE D

| The rate of metabolism (k) in Rat whole blood. | |
|---|---|
| Compound | k |
| A (PF-06463922) | −0.07473 |
| 6 | 0.61694 |
| 10 | 0.07435 |

Compound 6 was found to have much larger K value than PF-06463922 and Compound 10. Faster metabolism may result in much less toxicity for chemical compounds in a test subject.

Solubility Measurement:

Preparation of reference standard solution: 2 mg of Compound A or Compound 6 was added individually to 100 mL volumetric flask each. The compound was diluted with acetonitrile to 100 mL.

Preparation of sample solution: 2 mg of Compound A or Compound 6 was added individually to 2 mL eppendorf tube (EP), followed by addition of 1 mL of pH 7.0 or 10.0 buffer solution (20 mM). The solution was shook for 2 minutes and left for 30 minutes at 25° C. After standing for 30 minutes, precipitate was formed in the bottom of the EP. The solutions was filtered through 0.2 μm membrane filter, and then diluted by 50 times with water.

The standard and sample solutions were injected into the HPLC on a Shim-Pack CLC-ODS C18 column (150 mm×6.0 mm, 5 um) with the same volume. The mobile phase consisted of acetonitrile with 2% trichloromethane-20 mM $KH_2PO_4$ buffer (pH=7.0) at a flow rate of 1 mL/minutes (40:60). The detection wavelength is at 264 nm. Calculation: solubility of sample=the concentration of standard×Area of sample×50/Area of standard. Compound 6 had a similar solubility to Compound A at pH=10.0, but had much higher solubility than compound A at pH=7.0.

TABLE E

| Solubility of Compounds of the invention | | |
|---|---|---|
| | Compound A (PF-06463922 | Compound 6 |
| Solubility at pH 7.0 | 0.029 mg/mL | 0.091 mg/mL |
| Solubility at pH 10.0 | 0.028 mg/mL | 0.036 mg/mL |

What is claimed is:

1. A compound according to formula I:

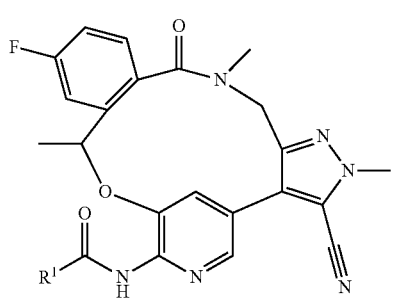

or a pharmaceutically acceptable salt, solvate or an enantiomer thereof, wherein $R^1$ is $C_{1-6}$ alkyl, or $NH_2(R^2R^3)C$—; and $R^2$ and $R^3$ are independently H or $C_{1-6}$ alkyl.

2. The compound according to claim 1, the compound being selected from the group consisting of:

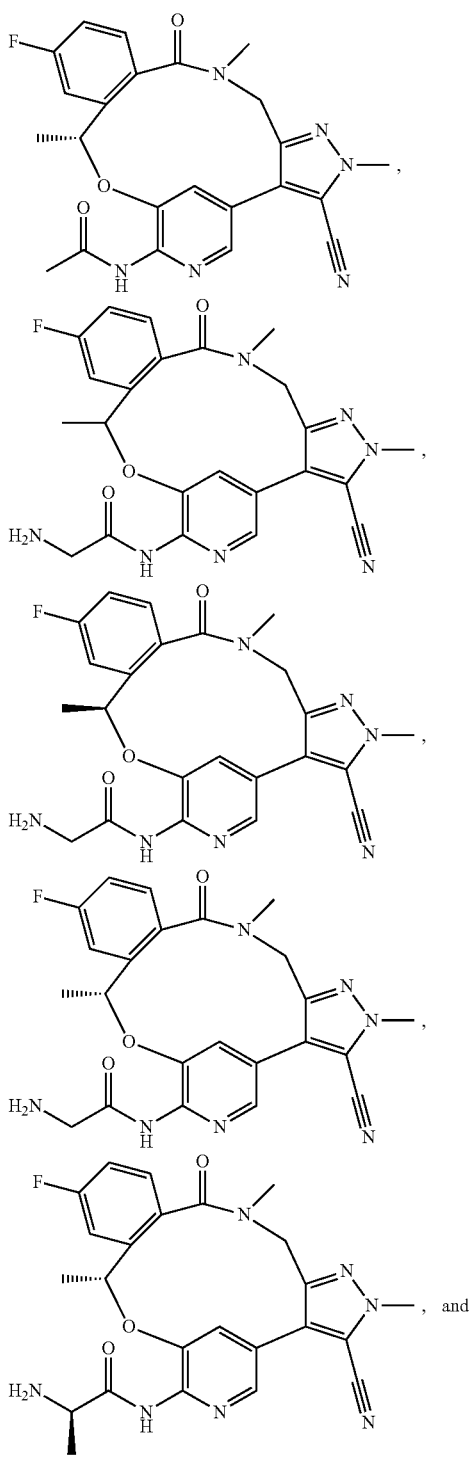

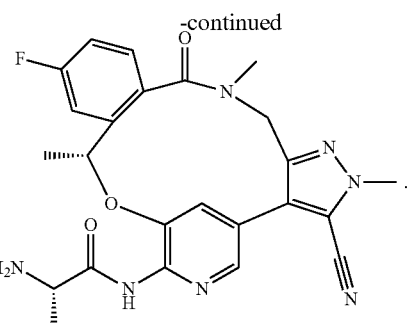

3. A pharmaceutical composition comprising a compound of claim 1 and a pharmaceutically acceptable carrier.

4. The pharmaceutical composition according to claim 3, further comprising one or more anti-cancer agents for treating neoplasia.

5. A method of treating a disease in an individual, comprising: administering to the individual a therapeutically effective amount of a pharmaceutical composition comprising a compound of claim 1, wherein the disease is lung cancer.

6. A compound according to formula Ia:

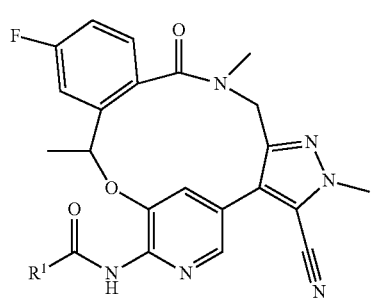

Ia or a pharmaceutically acceptable salt, solvate or an enantiomer thereof, wherein $R^1$ is $NH_2(R^2R^3)C-$; and $R^2$ and $R^3$ are independently H or $C_{1-6}$ alkyl.

7. A pharmaceutical composition comprising a compound of claim 6 and a pharmaceutically acceptable carrier.

* * * * *